(12) United States Patent
Hirata

(10) Patent No.: US 10,314,604 B2
(45) Date of Patent: Jun. 11, 2019

(54) ENDOSCOPIC TREATMENT INSTRUMENT AND ENDOSCOPE SYSTEM

(71) Applicant: OLYMPUS CORPORATION, Tokyo (JP)

(72) Inventor: Yasuo Hirata, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 318 days.

(21) Appl. No.: 15/139,512

(22) Filed: Apr. 27, 2016

(65) Prior Publication Data

US 2016/0235426 A1 Aug. 18, 2016

Related U.S. Application Data

(63) Continuation of application No. PCT/JP2014/067697, filed on Jul. 2, 2014.

(30) Foreign Application Priority Data

Oct. 29, 2013 (JP) ................................. 2013-224515

(51) Int. Cl.
*A61B 1/05* (2006.01)
*A61B 1/00* (2006.01)
(Continued)

(52) U.S. Cl.
CPC .......... *A61B 17/29* (2013.01); *A61B 1/00039* (2013.01); *A61B 1/00135* (2013.01);
(Continued)

(58) Field of Classification Search
CPC . A61B 1/0053; A61B 1/0057; A61B 1/00135; A61B 2017/00544; A61B 2017/2902; A61B 2017/2932; A61B 1/045
(Continued)

(56) References Cited

U.S. PATENT DOCUMENTS 4,832,473 A * 5/1989 Ueda .................... A61B 1/0053
359/367
4,991,564 A * 2/1991 Takahashi .......... A61B 1/00142
600/123
(Continued)

FOREIGN PATENT DOCUMENTS

JP 57-200141 A 12/1982
JP 1-94820 A 4/1989
(Continued)

OTHER PUBLICATIONS

International Search Report dated Aug. 26, 2014 received in International Application No. PCT/JP2014/067697.

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

A treatment instrument apparatus, which is an endoscopic treatment instrument, includes a sheath having an opening in a distal end; an actuator placed in the sheath and driven by a gas supplied via a tube; a treatment unit connected with the actuator by a wire and placed on a distal end side of the opening of the sheath; and an opening and closing switch, which is an operation portion used for an operation of supplying the gas into the sheath and supplying the gas to the actuator.

13 Claims, 8 Drawing Sheets

(51) Int. Cl.
*A61B 17/29* (2006.01)
*A61B 1/018* (2006.01)
*A61B 17/00* (2006.01)
*A61B 1/045* (2006.01)
*A61B 90/00* (2016.01)

(52) U.S. Cl.
CPC ............. *A61B 1/018* (2013.01); *A61B 1/045* (2013.01); *A61B 1/05* (2013.01); *A61B 17/00234* (2013.01); *A61B 1/0014* (2013.01); *A61B 1/00045* (2013.01); *A61B 90/37* (2016.02); *A61B 2017/00296* (2013.01); *A61B 2017/00336* (2013.01); *A61B 2017/00477* (2013.01); *A61B 2017/00544* (2013.01); *A61B 2017/2902* (2013.01); *A61B 2017/2931* (2013.01); *A61B 2017/2947* (2013.01); *A61B 2017/2948* (2013.01)

(58) Field of Classification Search
USPC ........................................................ 600/104
See application file for complete search history.

(56) References Cited

U.S. PATENT DOCUMENTS

| | | | |
|---|---|---|---|
| 8,933,387 B2* | 1/2015 | Iida | A61B 34/70 250/221 |
| 2002/0013570 A1* | 1/2002 | Ruegg | A61B 1/00087 606/1 |
| 2003/0216749 A1 | 11/2003 | Ishikawa et al. | |
| 2006/0235368 A1* | 10/2006 | Oz | A61B 10/06 606/1 |
| 2009/0112229 A1* | 4/2009 | Omori | A61B 17/29 606/130 |
| 2011/0039967 A1* | 2/2011 | Wilson | C08G 18/3851 521/164 |
| 2011/0105846 A1* | 5/2011 | Yoshie | A61B 1/0053 600/158 |
| 2011/0301414 A1* | 12/2011 | Hotto | A61B 1/00009 600/114 |
| 2013/0047770 A1* | 2/2013 | Iida | G01D 5/268 74/490.01 |
| 2013/0053643 A1* | 2/2013 | Yoshida | A61B 1/00006 600/114 |

FOREIGN PATENT DOCUMENTS

| | | |
|---|---|---|
| JP | 6-343643 A | 12/1994 |
| JP | 2005-95673 A | 4/2005 |
| JP | 2006-500986 A | 1/2006 |
| JP | 2010-220685 A | 10/2010 |
| WO | WO 2004/028585 A2 | 4/2004 |

* cited by examiner

ENDOSCOPIC TREATMENT INSTRUMENT AND ENDOSCOPE SYSTEM

CROSS REFERENCE TO RELATED APPLICATION

This application is a continuation application of PCT/JP2014/067697 filed on Jul. 2, 2014 and claims benefit of Japanese Application No. 2013-224515 filed in Japan on Oct. 29, 2013, the entire contents of which are incorporated herein by this reference.

BACKGROUND OF THE INVENTION

1. Field of the Invention

The present invention relates to an endoscopic treatment instrument and an endoscope system, and more particularly, to an endoscopic treatment instrument and an endoscope system which are equipped with an actuator driven by gas.

2. Description of the Related Art

Conventionally, endoscope apparatuses are used widely in medical fields and industrial fields. Endoscopic treatment instruments are sometimes used together with endoscopes.

For example, in the industrial field, treatment instruments are used together with endoscopes in endoscopic examinations to collect foreign matter in test objects or to sample substances in piping.

For example, Japanese Patent Application Laid-Open Publication No. 2010-220685 discloses a manipulator equipped with a grasping portion used to grasp an object and the like, wherein a pneumatic actuator is housed in a tubular portion having flexibility, to cause the grasping portion to perform an opening and closing action.

Because the endoscopic examination is conducted by inserting an insertion portion of the endoscope in the test object, desirably the endoscopic treatment instrument has a small-diameter tubular member as with the insertion portion of the endoscope.

However, a configuration of the manipulator according to the above proposal has a problem in that plural pneumatic actuators are mounted in a flexible tube portion, increasing an outside diameter of the manipulator.

Thus, an object of the present invention is to provide an endoscopic treatment instrument and endoscope system which are equipped with an actuator driven by gas and capable of reducing a diameter.

SUMMARY OF THE INVENTION

An endoscopic treatment instrument according to one aspect of the present invention includes: a sheath having an opening in a distal end; an actuator placed in the sheath and driven by a gas supplied via a tube; a treatment unit connected with the actuator by a linear member and placed on a distal end side of the opening of the sheath; and an operation portion used for an operation of supplying the gas to a space between an inner side of the sheath and an outer side of the actuator as well as supplying the s to the actuator.

An endoscope system according to one aspect of the present invention includes: the endoscopic treatment instrument according to the present invention; an endoscope apparatus provided with an insertion portion and a main body portion; and a guide apparatus shaped like a conduit, configured to have flexibility, and provided with first and second insertion channels through which the sheath of the endoscopic treatment instrument and the insertion portion of the endoscope apparatus are passed, respectively.

An endoscope system according to one aspect of the present invention includes: the endoscopic treatment instrument according to the present invention; and an endoscope apparatus provided with an insertion portion and a main body portion, wherein the sheath of the endoscopic treatment instrument is configured to be able to be passed through a treatment instrument insertion channel of the insertion portion of the endoscope apparatus.

DETAILED DESCRIPTION OP THE PREFERRED EMBODIMENT

Figure 1:
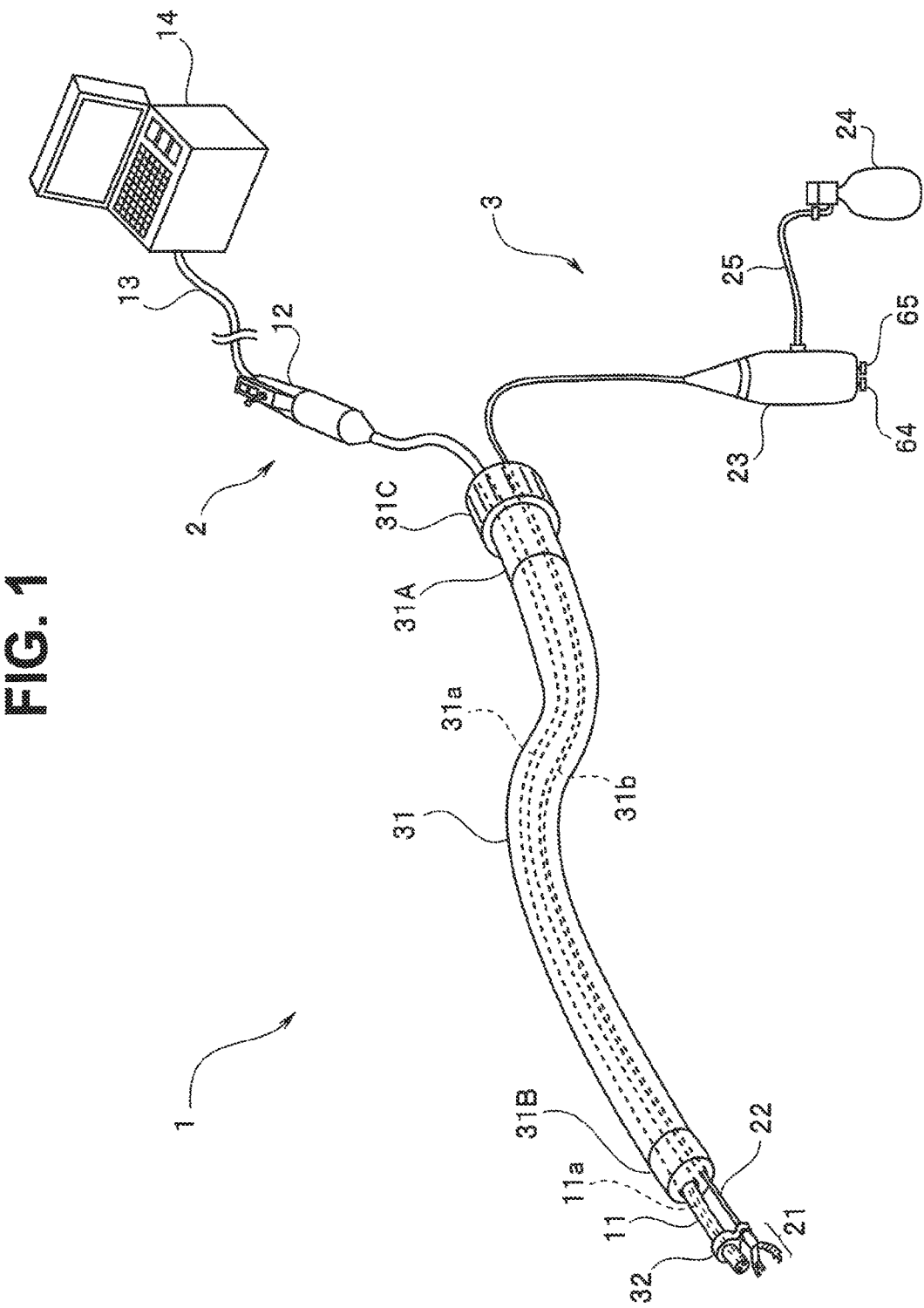
FIG. 1 is a configuration diagram showing an overall configuration of an endoscope system according to an embodiment of the present invention.

An embodiment of the present invention will be described below with reference to the drawings.

Note that in the drawings referred to in the following description, to make each component large enough to be recognized, scaling is varied from component to component, and that the present invention is not limited only to quantities, shapes, size ratios, and relative positional relationships of the components shown in the drawings.

(Configuration of Endoscope System)

FIG. 1 is a configuration diagram showing an overall configuration of an endoscope system according to the present embodiment. An endoscope system 1 includes an endoscope apparatus 2 and a treatment instrument apparatus 3.

The endoscope apparatus 2 includes an elongated insertion portion 11 having flexibility, an endoscope operation portion 12 connected to a proximal end side of the insertion portion 11, and a main body portion 14 connected with the endoscope operation portion 12 via a cable 13. An image pickup device is placed in a distal end portion of the insertion portion 11 to pick up images of an object and an image signal resulting from the image pickup is supplied to the main body portion 14 via the endoscope operation portion 12.

The endoscope operation portion 12 is provided with a joystick and various boutons for use to specify various functions including bending operation, image freeze, and release. The main body portion 14 is provided with input devices such as a keyboard and various boutons as well as a display apparatus and can receive the image signal and output an endoscopic image to the display apparatus.

The main body portion 14 contains a central processing unit (CPU) and a memory device. The endoscope apparatus 2 is configured to achieve any of various functions including displaying or recording an endoscopic image when the central processing unit (CPU) executes a processing program corresponding to a command issued by a user via the endoscope operation portion 12 or the like.

The treatment instrument apparatus 3 is an endoscopic treatment instrument made up of a treatment unit 21 which is forceps configured to collect foreign matter and carry out various other treatments, a sheath 22 which is an insertion tube portion installed consecutively with the treatment unit 21 and provided with flexibility and a treatment instrument operation portion 23 connected with a proximal end portion of the sheath 22. The treatment instrument operation portion 23 is connected with a gas cylinder (e.g., liquefied carbon dioxide cylinder) 24 configured to supply air 24 through a tube 25. Note that a compressor may be connected instead of the gas cylinder 24.

As described later, by operating two control buttons provided on the treatment instrument operation portion 23 the user can perform an opening and closing action of the treatment unit 21, which is forceps.

In the example shown in FIG. 1, the insertion portion 11 of the endoscope apparatus 2 and the sheath 22 of the treatment instrument apparatus 3 are passed through an endoscope channel 31a and a treatment instrument channel 31b, respectively, provided in a guide apparatus 31 shaped like a conduit and configured to have flexibility.

The insertion portion 11 and sheath 22 are inserted into the endoscope channel 31a and treatment instrument channel 31b, respectively, from a side of the pipe sleeve portion 31A provided on a proximal end side of the guide apparatus 31 and protruded from a pipe sleeve portion 31B provided on a distal end side of the guide apparatus 31. A fixing member 31C is provided on the pipe sleeve portion 31A to fix the insertion portion 11 and sheath 22 to the guide apparatus 31. When the fixing member 31C is turned in a predetermined direction around an axis of the guide apparatus 31, the fixing member 31C tightens the insertion portion 11 and sheath 22 from outside, fixing the insertion portion 11 and sheath 22 to the guide apparatus 31.

The distal end portion of the insertion portion 11 of the endoscope apparatus 2 and a distal end portion of the sheath 22 of the treatment instrument apparatus 3 are fixed to each other by the fixing member 32.

The user can bring the distal end portion of the insertion portion 11 of the endoscope apparatus 2 and the distal end portion of the sheath 22 of the treatment instrument apparatus 3 protruding from a distal end portion of the guide apparatus 31 to a desired position in the test object and carry out predetermined treatment such as collecting foreign matter using the treatment unit 21 by displaying endoscopic images of an area to be examined in the main body portion 14 or watching the endoscopic images.

Thus, the endoscope system 1 includes the treatment instrument apparatus 3 which is an endoscopic treatment instrument, the endoscope apparatus 2 provided with the insertion portion 11 and main body portion 14, the treatment instrument channel 31b and endoscope channel 31a through which the sheath 22 of the treatment instrument apparatus 3 and the insertion portion 11 of the endoscope apparatus 2 are passed, respectively, and the guide apparatus 31 shaped like a conduit and configured to have flexibility.

Note that although the sheath 22 which is an insertion tub portion of the treatment instrument apparatus 3 is used by being passed through the treatment instrument channel 31b of the guide apparatus 31 herein, the sheath 22 may be used by being passed through a treatment instrument insertion channel 11a provided in the insertion portion 11 of the endoscope apparatus 2. In that case, the endoscope system 1 includes the treatment instrument apparatus 3 which is an endoscopic treatment instrument, and the endoscope apparatus 2 provided with the insertion portion 11 and main body portion 14, wherein the sheath 22 of the treatment instrument apparatus 3 can be passed through the treatment instrument insertion channel of the insertion portion 11 of the endoscope apparatus 2.

(Configuration of Treatment Instrument)

Figure 2:
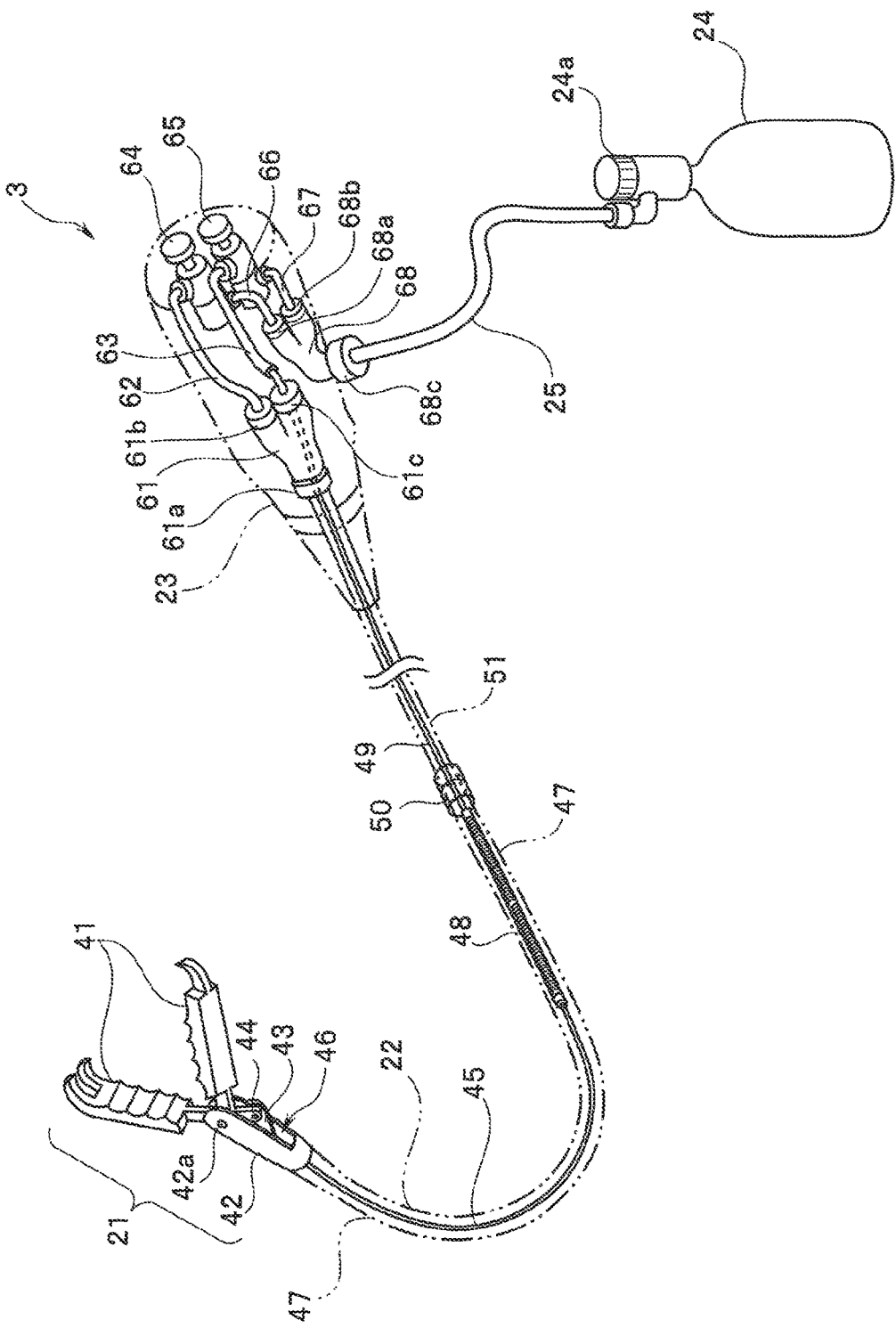
FIG. 2 is a configuration diagram showing an overall configuration of a treatment instrument apparatus 3 according to the embodiment of the present invention.

FIG. 2 is a configuration diagram showing an overall configuration of the treatment instrument apparatus 3. Note that in FIG. 2, the treatment unit 21 of the treatment instrument apparatus 3 is shown by being enlarged particularly.

As shown in FIG. 2, the treatment unit 21 provided in a distal end portion of the treatment instrument apparatus 3, which is an endoscopic treatment instrument, includes two arm members 41. In portions close to a proximal end side, the two arm members 41 are pivotally supported by an axial member 42a provided on a support member 42. The two arm members 41 make up a pinching unit which can perform an opening and closing action by being brought close to, or spaced away from, each other when an actuator 48 described later operates.

Respective distal end portions of two link members 43 are connected to proximal end portions of the arm members 41 in such a way as to be pivotable around a pivot axis of an axial member 44.

The support member 42 includes a slit portion 46 formed along an axial direction. The respective proximal end portions of the two arm members 41 described above as well as the above-described two link members 43 connected to the two arm members 41 are disposed in the slit portion 46.

Figure 4:
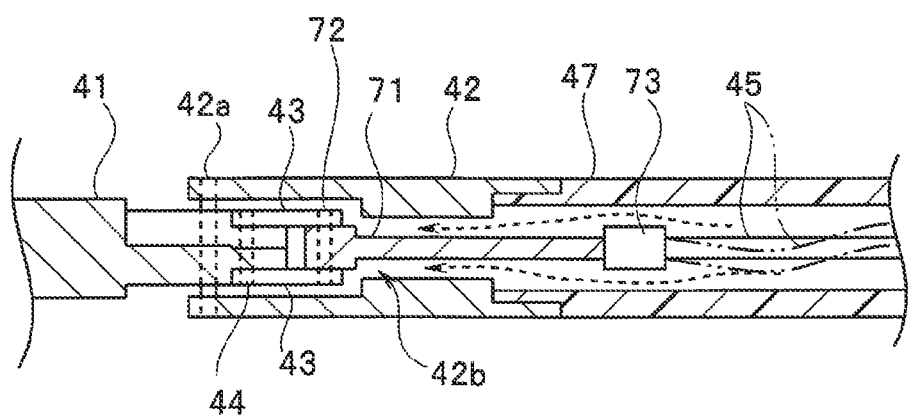
FIG. 4 is a sectional view of a treatment unit 21 according to the embodiment of the present invention.

A hole 42b is formed in a proximal end portion of the support member 42, and a rod 71 described later is passed through the hole 42b (FIG. 4).

A wire 45 which is a linear member is passed through a sheath member 47 which is tubular and made of resin. The sheath member 47 makes up part of the sheath 22 on a distal end side. A distal end of the wire 45 is connected to a proximal end portion of the rod 71 passed through the hole 42b in the support member 42. A proximal end portion of the wire 45 is connected and fixed to a distal end portion of the actuator 48.

The actuator 48 is also elongated in shape and is housed and placed in the sheath member 47. The actuator 48 is an artificial muscle configured to pull the wire 45 so that the two arm members 41 perform a closing action of the opening and closing action.

The distal end portion of the actuator 48 is connected to the proximal end portion of the wire 45 while a proximal end portion of the actuator 48 is connected to one end of a tube 49 to supply air, which is a gas. The tube 49 allows the air passing through the tube 49 to be supplied into the actuator 48.

Note that the actuator 48 here is a so-called McKibben soft actuator in which a rubber tube (silicon, urethane, or the like) having elasticity is provided in a mesh made of PET or formed of fibers such as a polyamide strand or stainless steel line wires. The actuator 20 is configured such that when the rubber tube is inflated and deflated by being pressurized by supplied air a fiber mesh covering the rubber tube causes the actuator 20 to contract, allowing a longitudinal length to be varied.

As described above, the treatment instrument apparatus 3 includes the sheath 22 having an opening in a distal end; the actuator 48 placed in the sheath 22 and driven by a gas supplied from the proximal end side via the tube 49: and the treatment unit 21 connected with the actuator 48 by the wire 45, which is a linear member, and placed on a distal end side of the opening of the sheath 22.

A proximal end portion of the tubular sheath member 47 is coupled to a distal end portion of the tubular resin-made sheath member 51 via a connection ring 50. The sheath member 51 makes up part of the sheath 22 on the proximal end side. A proximal end portion of the sheath member 51 is connected to the treatment instrument operation portion 23.

Figure 3:
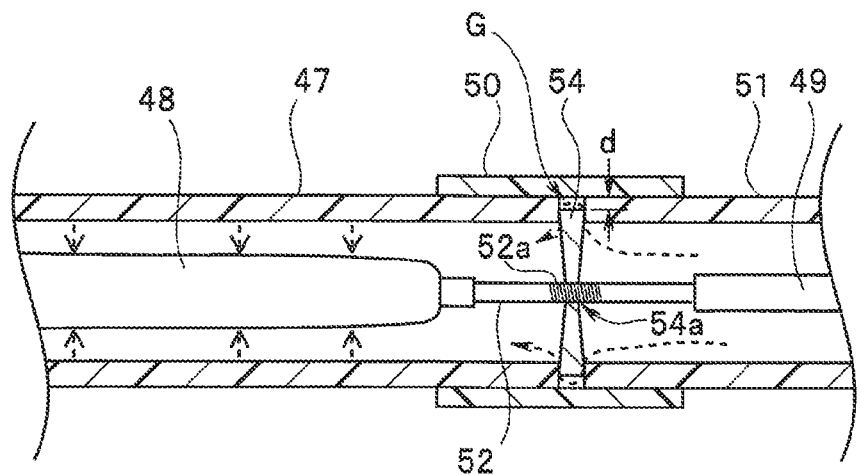
FIG. 3 is a sectional view of a connecting portion between sheath members 47 and 51 connected by a connection ring 50 in the embodiment of the present invention.

FIG. 3 is a sectional view of a connecting portion between the sheath members 47 and 51 connected by the connection ring 50.

A pipe sleeve 52 tubular in shape is fixed to the proximal end portion of the actuator 48, and a tube 53 is fitted around a proximal end portion of the pipe sleeve 52. Air can be supplied into the actuator 48 from the tube 49.

A threaded portion 52a is provided on an outer circumferential face of the pipe sleeve 52. An annular fixing member 54 can be attached to the pipe sleeve 52. The fixing member 54 is made, for example, of metal, a hole 54a is formed in a central portion of the fixing member 54, and a threaded portion to be screwed onto the threaded portion 52a of the pipe sleeve 52 is formed on an inner circumferential face of the hole 54a. The fixing member 54 is shaped to decrease in thickness toward the hole 54a in the central portion from an outer circumferential portion.

Note that the fixing member 54 may be shaped like a disk with a fixed thickness.

The fixing member 54 can be fixed to the pipe sleeve 52 by screwing the threaded portion 52a of the pipe sleeve 52 into the hole 54a in the fixing member 54.

Axial position adjustments in the sheath member 47 of the actuator 48 are made by adjusting a screwing position of the fixing member 54 screwed onto the pipe sleeve 52.

As shown in FIG. 3, with the fixing member 54 sandwiched between an end face of the sheath member 47 on the proximal end side and an end face of the sheath member 51 on the distal end side, the two end faces of the sheath members 47 and 51 are connected by being covered with the connection ring 50, which is a cover member. An outside diameter of the fixing member 54 is larger than inside diameters of the two sheath members 47 and 51, but smaller than an inside diameter of the connection ring 50.

When the connection ring 50 is attached after applying an adhesive to outer circumferential faces of the sheath members 47 and 51, the connection ring 50 is fixed firmly to the sheath members 47 and 51 on opposite sides of the fixing member 54. As a result, the proximal end portion of the actuator 48 is fixed to the connection ring 50. Note that a configuration in which no adhesive is applied may be used by making the inside diameter of the connection ring 50 a little smaller, fitting the sheath member 47 and sheath member 51 in the connection ring 50, and thereby fixing the sheath members 47 and 51 to the connection ring 50.

Here, because the outside diameter of the fixing member 54 is smaller than outside diameters of the two sheath members 47 and 51, when the sheath members 47 and 51 are connected, a gap G having a pr determined distance d is formed between an inner circumferential face of the connection ring 50 and outer circumferential face of the fixing member 54 as shown in FIG. 3. The gap is formed along an outer circumferential edge of the annular fixing member 54, and consequently when pressure in the sheath member 51 increases, the air in the sheath member 51 flows into the sheath member 47 through the gap G as indicated by dotted lines.

Also, since the fixing member 54 is shaped to decrease in thickness toward the hole 54a in the central portion from the outer circumferential portion, the air in the sheath member 51 flows more readily into the sheath member 47 through the gap G.

As described above, the sheath 22 includes the first sheath member 47, the second sheath member 51, and the fixing member 54, which is a member sandwiched between the first sheath member 47 and second sheath member 51. The actuator 48 is placed in the first sheath member 47. The gas in the sheath 22 can be supplied to the distal end side of the sheath 22 via the gap G formed between the fixing member 54 sandwiched between the first sheath member 47 and second sheath member 51 and the connection ring 50, which is the cover member covering the first sheath member 47 and second sheath member 51. Also, by assuming that the outside diameter of the fixing member 54 is substantially equal to the inside diameter of the sheath members 47 and 51, the outside diameter of the fixing member 54 may partially be made smaller than the inside diameter of the sheath members 47 and 51 at plural locations.

Returning to FIG. 2, the proximal end portion of the sheath member 51 is connected to a first connection portion 61a of a joint 61 provided in the treatment instrument operation portion 23. The joint 61 has three connection portions. A second connection portion 61b and third connection portion 61c of the joint 61 are connected to an opening switch 64 for opening operation of the treatment unit 21 and closing switch 65 for closing operation of the treatment unit 21 via conduits 62 and 63, respectively. The opening and closing switches 64 and 65 are operation portions provided with a mechanism configured to supply air to the conduits 62 and 63, respectively, while being pressed and discharge air when not pressed.

The opening switch 64 and closing switch 65 are connected to a first connection portion 68a and second connection portion 68b of a joint 68 via conduits 66 and 67, respectively. The joint 68 also has three connection portions, and a third connection portion 68c is located outside the treatment instrument operation portion 23 and connected to one end of the tube 25. Another end of the tube 25 is connected to the gas cylinder 24, which is an air supply source, allowing air to be jetted from a distal end portion of the tube 25. Note that the gas cylinder 24 is provided with a regulator 24a. That is, the opening switch 64 and closing switch 65 make up an operation portion operated to supply gas into the sheath 22 and supply gas to the actuator 48.

FIG. 4 is a sectional view of the treatment unit 21. As shown in FIG. 4, the rod 71 is passed through the hole 42b in the support member 42 along the axial direction. Proximal end portions of the two link members 43 are connected with a distal end portion of the rod 71 in such a way as to be pivotable around a pivot axis of an axial member 72. The proximal end portion of the rod 71 is connected to a distal end portion of the wire 45, which is a linear member, via a coupling member 73.

(Operation)

Next, the opening and closing action of the treatment unit 21 of the treatment instrument apparatus 3 will be described.

When the user presses the opening switch 64, the air supplied from the gas cylinder 24 through the tube 25, joint 68, and conduit 66 is discharged into the sheath member 51 through the conduit 62 and joint 61.

Pressurized air in the sheath member 51 is discharged into the sheath member 47 through the gap G inside the connection ring 50 as shown in FIG. 3.

The air in the sheath member 47 presses the actuator 48 from outside as indicated by dotted lines in FIG. 3, pushes out the wire 45 in the sheath member 47 toward a distal end portion of the sheath member 47 via flow of air, and furthermore, pushes out the rod 71 in the support member 42 to the distal end side by means of air pressure as indicated by dotted lines in FIG. 4.

The wire 45 remains slack in the sheath member 47 as indicated by chain double-dashed lines in FIG. 4 when not pulled by the actuator 48, but is pushed out toward the distal end portion of the sheath member 47 by air when the opening switch 64 is pressed. Consequently, the proximal end portions of the two link members 43 move to the distal end side causing the two arm members 41 to move away from each other and thereby open the treatment unit 21.

When the user presses the closing switch 65, the air supplied from the gas cylinder 24 through the tube 25, joint 68, and conduit 67 is discharged into the tube 49 through the conduit 63 and joint 61.

Pressurized air in the tube 49 is discharged into the actuator 48 through the pipe sleeve 52.

When air is supplied into the actuator 48, the actuator 48 expands and contracts toward the proximal end side, thereby pulling the wire 45. When the wire 45 is pulled, the proximal end portions of the two link members 43 are moved to the proximal end side by the rod 71, causing the two arm members 41 to move close to each other and thereby close the treatment unit 21.

Thus, the opening and closing action of the treatment unit 21 is performed by a linkage mechanism configured to convert advancing and retracting action of the wire 45, which is a linear member running along an axial direction of sheath 22, into the opening and closing action.

Note that whereas the opening and closing switches 64 and 65 herein have a mechanism configured to supply air to the conduits 62 and 63, respectively, while being pressed and discharge air when not pressed, if the opening and closing switches 64 and 65 employ solenoid valves, the opening and closing switches 64 and 65 may be operation portions provided with a mechanism configured to close the solenoid valves to maintain pressure in the conduits 62 and 63 when the opening and closing switches 64 and 65 are pressed.

Furthermore, whereas in the above example, the treatment unit 21 opens when air is supplied into the sheath member 47 and closes when air is supplied to the actuator 48, the linkage mechanism including the two link members 43 may be changed so as to set advancing and retracting action of the rod 71 in the axial direction such that the treatment unit 21 will close when air is supplied into the sheath member 47 and open when air is supplied to the actuator 48. In that case, if for example, a fixing section of the actuator 48 is set on the side of a link 42a, the treatment instrument 21 opens when air is supplied to the actuator 48. Also, if air is caused to flow inward from outside by doubling the sheath member 47 and caused to flow from the distal end side to the proximal end side by folding back the sheath member 47 at the distal end, the treatment instrument 21 closes when air is supplied into the sheath member 47.

Thus, the treatment instrument apparatus 3 described above makes it possible to implement an endoscopic treatment instrument equipped with an actuator driven by gas and capable of reducing a diameter.

Furthermore, similar effects can be achieved even when the rod 71, coupling member 73, and wire 45 are set to be equal in outside diameter without any height difference.

Next, modifications will be described.

(Modification 1)

Although in the embodiment described above, air is supplied from the sheath member 51 to the sheath member 47 through the gap G formed between the inner circumferential face of the connection ring 50 and outer circumferential face of the fixing member 54, air may be supplied from the sheath member 51 to the sheath member 47 through a hole provided in the fixing member.

Figure 5:
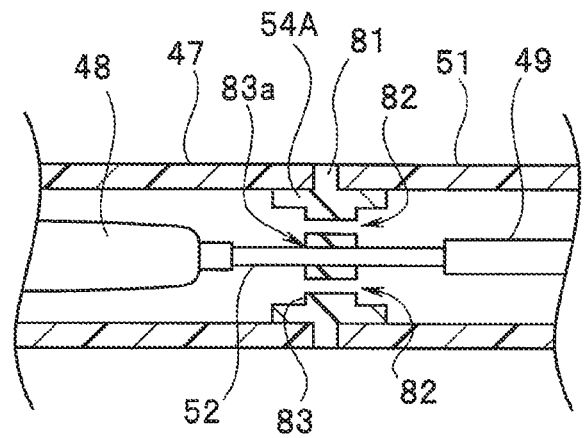
FIG. 5 is a sectional view of a connecting portion between the sheath members 47 and 51 connected by a fixing member 54A in modification 1 of the embodiment of the present invention.

FIG. 5 is a sectional view of a connecting portion between the sheath members 47 and 51 connected by a fixing member 54A in modification 1. The fixing member 54A is shaped like a pipe and provided with a ring-shaped protrusion 81 in a central portion, protruding radially outward. Sandwiching the protrusion 81, the sheath members 47 and 51 are fitted over a stepped portion and fixed by adhesive, where the stepped portion is formed by the protrusion 81 of the fixing member 54A.

The fixing member 54A has a partition wall 83 in a central portion, where the partition wall 83 is provided with plural air vents 82. Furthermore, the partition wall 83 has a hole 83a in a central portion and a thread is formed in the hole 83a to screw in and fix the pipe sleeve 52.

Through the plural air vents 82 formed in the partition wall 83 of the fixing member 54A, air is supplied from the sheath member 51 to the sheath member 47.

As described above, the sheath 22 includes the first sheath member 47, the second sheath member 51, and the fixing member 54A, which is a member sandwiched between the first sheath member 47 and second sheath member 51, and the gas in the sheath 22 can be supplied to the distal end side of the sheath 22 through the one or more air vents 82 formed in the fixing member 54A sandwiched between the first sheath member 47 and second sheath member 51.

Note that although a plural air vents 82 are formed in the fixing member 54A herein, a single air vent 82 may be sufficient depending on size of the air vent 82.

Figure 6:
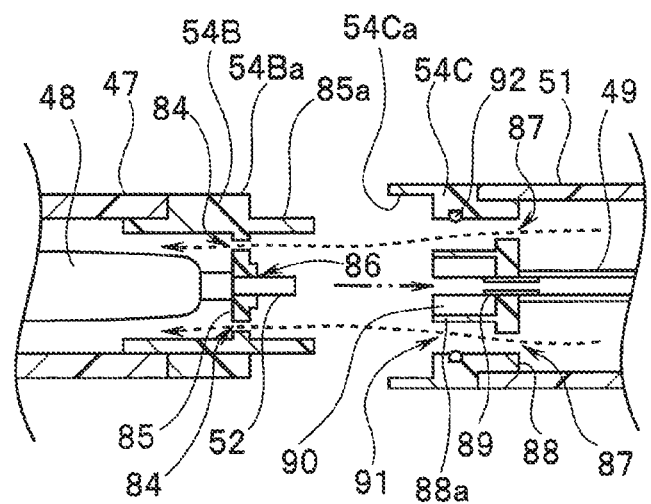
FIG. 6 is a sectional view of a connecting portion between the sheath members 47 and 51 connected by two fixing members 54B and 54C in another example of modification 1 of the embodiment of the present invention.

As another example of modification 1, air may be supplied from the sheath member 51 to the sheath member 47 using a configuration such as shown in FIG. 6.

FIG. 6 is a sectional view of a connecting portion between the sheath members 47 and 51 connected by two fixing members 54B and 54C in another example of modification 1.

The fixing member 54B is attached to the proximal end portion of the sheath member 47 and fixed to the sheath member 47 by adhesive. On the other hand, the fixing member 54C is attached to the distal end portion of the sheath member 51 and fixed to the sheath member 51 by adhesive.

The fixing member 54B has a pipe-like shape and contains a partition wall 85 provided with plural air vents 84. The partition wall 85 has a hole 86 formed in a central portion to screw in and fix the pipe sleeve 52 of the actuator 48. An annular extending portion 85a is formed on a face of the partition wall 85 on the proximal end side, extending out to the proximal end side.

The fixing member 54C has a pipe-like shape and includes a partition wall 88 provided with plural air vents 87. A hole is formed in a central portion of the partition wall 88. A pipe 89 is fitted in the hole, and a tube 49 is attached and fixed to a proximal end portion of the pipe 89. As shown in FIG. 6, around the hole in which the pipe 89 is fitted an annular protrusion 88a is formed, protruding toward the distal end side from the partition wall 88.

A rubber member 90, which is a pipe-shaped elastic member, is provided. inside the protrusion 88a. A distal end portion of the pipe 89 is inserted and fixed in a hole in the rubber member 90. The pipe-shaped rubber member 90 is provided in a concave portion of the annular protrusion 88a. The hole in the pipe-shaped rubber member 90 is large enough to allow the pipe sleeve 52 to fit in and seal the hole.

The plural air vents 87 are formed around the protrusion 88a of the partition wall 88. Furthermore, a concave portion 91 in which the annular extending portion 85a of the fixing member 54B is fitted is formed on a distal end side of the fixing member 54C. An O-shaped ring 92 fitted in a groove is provided in an inner circumferential face of the concave portion 91.

A thread is formed in an inner circumferential face 54Ca on the distal end side of the fixing member 54C and a thread is formed also on an outer circumferential face 54Ba on a proximal end side of the fixing member 54B.

As the thread formed in the inner circumferential face 54Ca on the distal end side of the fixing member 54C is screwed onto the thread formed on the outer circumferential face 54Ba on a proximal end side of the fixing member 54B with the fixing members 54B and 54C placed close to each other such that the extending portion 85a of the fixing member 54B will fit in the concave portion 91 and that the pipe sleeve 52 will fit in the hole in the rubber member 90 the fixing members 54B and 54C are connected with each other.

With the fixing members 54B and 54C connected in this way, the air supplied through the tube 49 is supplied to the actuator 48 in airtight condition by being sealed by the rubber member 90. Furthermore, the air in the sheath member 51 is supplied to the sheath member 47 through the plural air vents 87 and plural air vents 84.

As described above, the sheath 22 includes the first sheath member 47, the second sheath member 51, and a member which is a member sandwiched between the first sheath member 47 and second sheath member 51, and the gas in the sheath 22 can be supplied to the distal end side of the sheath 22, through one or more air vents 84 and 87 formed in the member sandwiched between the first sheath member 47 and second sheath member 51, where the member sandwiched between the first sheath member 47 and second sheath member 51 is made up of the fixing member 54B fixed to a proximal end portion of the first sheath member 47 and the second fixing member 54C fixed to a distal end portion of the second sheath member 51.

Thus, the configuration according to modification 1 also allows air to be supplied reliably from the sheath member 51 to the sheath member 47.

(Modification 2)

Whereas in the embodiment and modification 1 described above, when air is supplied into the sheath member 47 and the air is fed to a distal end side of the sheath member 47, the wire 45 and rod 71 are pushed out by the air, in modification 2, the wire 45 is further provided with an air receiving member configured to receive pressure of the air flowing through the sheath member 47.

Figure 7:
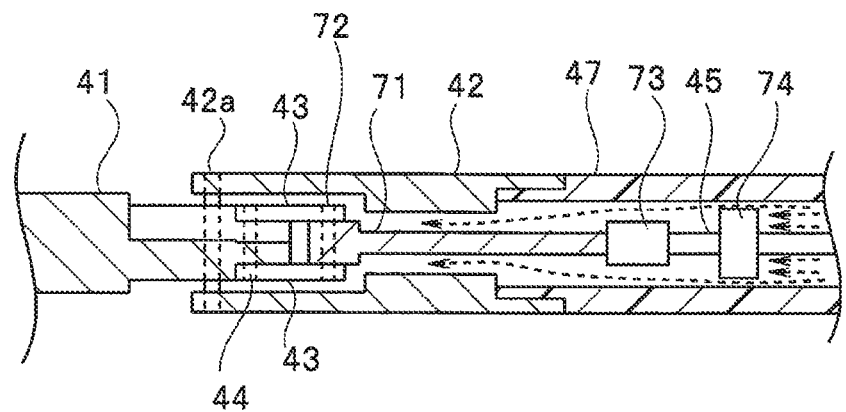
FIG. 7 is a sectional view of a treatment unit 21 according to modification 2 of the embodiment of the present invention.

FIG. 7 is a sectional view of a treatment unit 21 according to modification 2. As shown in FIG. 7, an air receiving member 74 is provided at a midpoint on the wire 45. The air receiving member 74 is a disk-shaped member with an outside diameter smaller than an inside diameter of the sheath member 47 and is fixed to the wire 45. That is, the air receiving member 74 is provided on an outer surface of the wire 45 which is a linear member and is a gas receiving unit configured to receive gas flowing from the proximal end side to distal end side of the sheath 22.

Air hits the air receiving member 74 and works to push out the air receiving member 74 to the distal end side of the sheath member 47. Thus, the air receiving member 74 allows action of the treatment unit 21, i.e., the opening action to be performed quickly.

Note that the air receiving member 74 does not have to be disk-shaped. Furthermore, the coupling member 73 may be allowed to combine a function of the air receiving member 74 by increasing an outside diameter of the coupling member 73.

(Modification 3)

Whereas in the embodiment and modifications 1 and 2 described above, the wire 45 and the like are pushed out to the distal end side of the sheath member 47 by the air sent to the sheath member 47, if pressure of the air is disturbed, excessive air pressure might be applied to the treatment unit 21. Therefore, an endoscopic treatment instrument according to modification 3 is designed such that the pressure in the sheath member 47 will fall when the wire 45 and the like move a predetermined amount.

Figure 8:
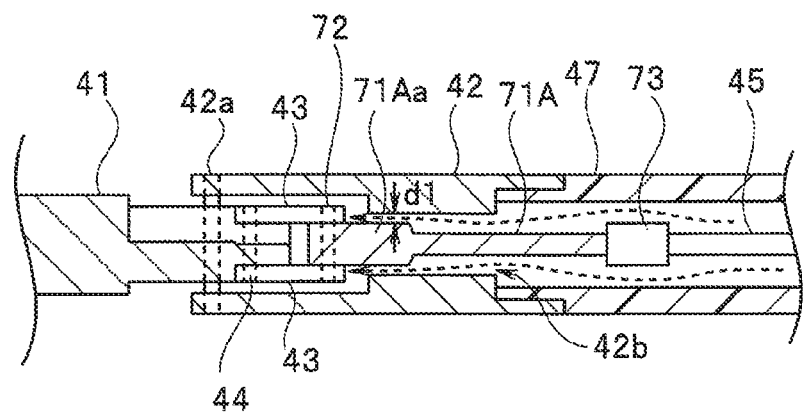
FIG. 8 is a partial sectional view of a treatment unit 21 in a state in which a wire 45 is being pulled by an actuator 48 in modification 3 of the embodiment of the present invention.

FIG. 8 is a partial sectional view of the treatment unit 21 in a state in which the wire 45 is being pulled by the actuator 48 in modification 3. In modification 3, the rod 71A passed through the hole 42b formed in the proximal end portion of the support member 42 has an expanded-diameter portion 71Aa on the distal end side. That is, the rod 71A, which is a rod member connected to the treatment unit 21 has the expanded-diameter portion 71Aa on the distal end side, where the expanded-diameter portion 71Aa has a diameter larger than an outside diameter of the rod 71A on the proximal end side.

When the closing switch 65 is pressed, air is sent to the actuator 48. Consequently, the actuator 48 operates and pulls the wire 45 to the proximal end side, bringing the treatment unit 21 into a closed state. FIG. 8 shows a state of the treatment unit 21 when the treatment unit 21 is closed. Note that size of the treatment instrument 21 or hole 42b may be changed so that part or all of the treatment instrument 21 will get into the hole 42b when the treatment instrument 21 is closed.

When the opening switch 64 is pressed in the state of FIG. 8, air is supplied into the sheath member 47, pushing out the wire 45 and rod 71A toward the treatment unit 21. In so doing, the air gets through a gap between an outer circumferential face of the expanded-diameter portion 71Aa and an inner circumferential face of the hole 42b formed in the proximal end portion of the support member 42, moving the rod 71A toward the treatment unit 21. That is, the expanded-diameter portion 71Aa is an air receiving unit configured to receive gas flowing from the proximal end side to distal end side of the sheath 22.

Figure 9:
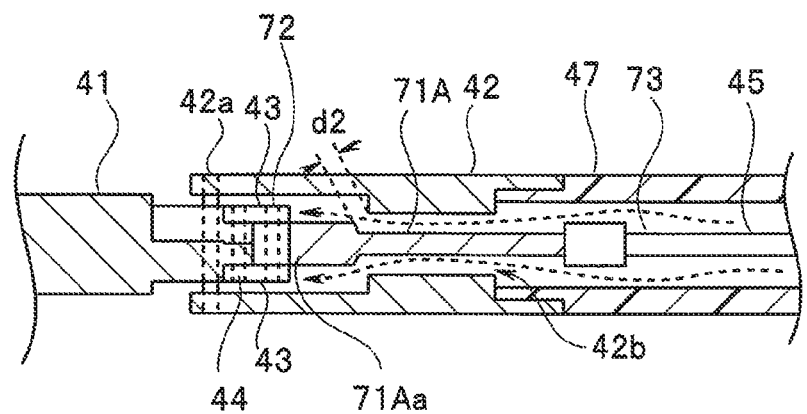
FIG. 9 is a partial sectional view of the treatment unit 21 in a state in which an expanded-diameter portion of a rod 71A comes out of a hole 42b, causing the treatment unit 21 to open, in modification 3 of the embodiment of the present invention.

As the rod 71A moves further toward the treatment unit 21, the expanded-diameter portion 71Aa of the rod 71A comes out of the hole 42b, and the treatment unit 21 opens at this time. FIG. 9 is a partial sectional view of the treatment unit 21 in a state in which the expanded-diameter portion 71Aa of the rod 71A comes out of the hole 42b, causing the treatment unit 21 to open.

When air is supplied into the sheath 22 and the rod 71A moves toward the distal end side, the expanded-diameter portion 71Aa of the rod 71A protrudes from an opening on a distal end side of the hole 42b, which is a passage hole through which the rod 71A is passed. When the expanded-diameter portion 71Aa comes out of the hole 42b, a distance between an outer circumferential face of the rod 71A, including the outer circumferential face of the expanded-diameter portion 71Aa, and the inner circumferential face of the hole 42b increases.

In FIG. 8, the distance of the gap between the outer circumferential face of the expanded-diameter portion 71Aa and inner circumferential face of the hole 42b is d1. In FIG. 9, a distance of maximum spacing between the outer circumferential face of the rod 71A, including the outer circumferential face of the expanded-diameter portion 71Aa, and the inner circumferential face of the hole 42b is d2. The expanded-diameter portion 71Aa is formed on the rod 71A such that d2 will be larger than d1.

Thus, when air is supplied to the sheath member 47 to open the treatment unit 21, since the distance of the gap between the outer circumferential face of the expanded-diameter portion 71Aa and inner circumferential face of the hole 42b is small at the beginning, a fast flow of air occurs in the sheath member 47. However, when the treatment unit 21 is in an open state, the gap between the outer circumferential face of the rod 71A and inner circumferential face of the hole 42b increases, causing the pressure in the sheath member 47 to fall compared to when the treatment unit 21 started to open, and consequently a gentle flow of air occurs.

As a result, after the treatment unit 21 opens, the pressure in the sheath member 47 falls, causing decreases in stresses applied to portions connected by the connection ring 50 and stresses applied to the axial member 42a and the like of the linkage mechanism of the treatment unit 21 by air from inside the sheath member 47.

Thus, according to modification 3, when the treatment unit 21 enters a predetermined state, unnecessary stresses are not applied to various members such as the treatment unit 21.

Also, measures may be taken to ensure that air will not leak from the gap between the rod 71A and hole 42b and that air will be released when the expanded-diameter portion 71Aa at a distal end of the rod 71A is pushed out of the hole 42b. This configuration allows a flow rate of the air to be reduced further.

Also, as shown in FIGS. 8 and 9, since stepped part on the proximal end side of the rod 71A is tapered, the rod 71A can enter the hole portion 42b easily.

(Modification 4)

Modification 4 provides an endoscopic treatment instrument having a structure which takes into consideration ease of assembly of the treatment instrument operation portion 23 according to the embodiment and modifications 1 to 3 described above.

Figure 10:
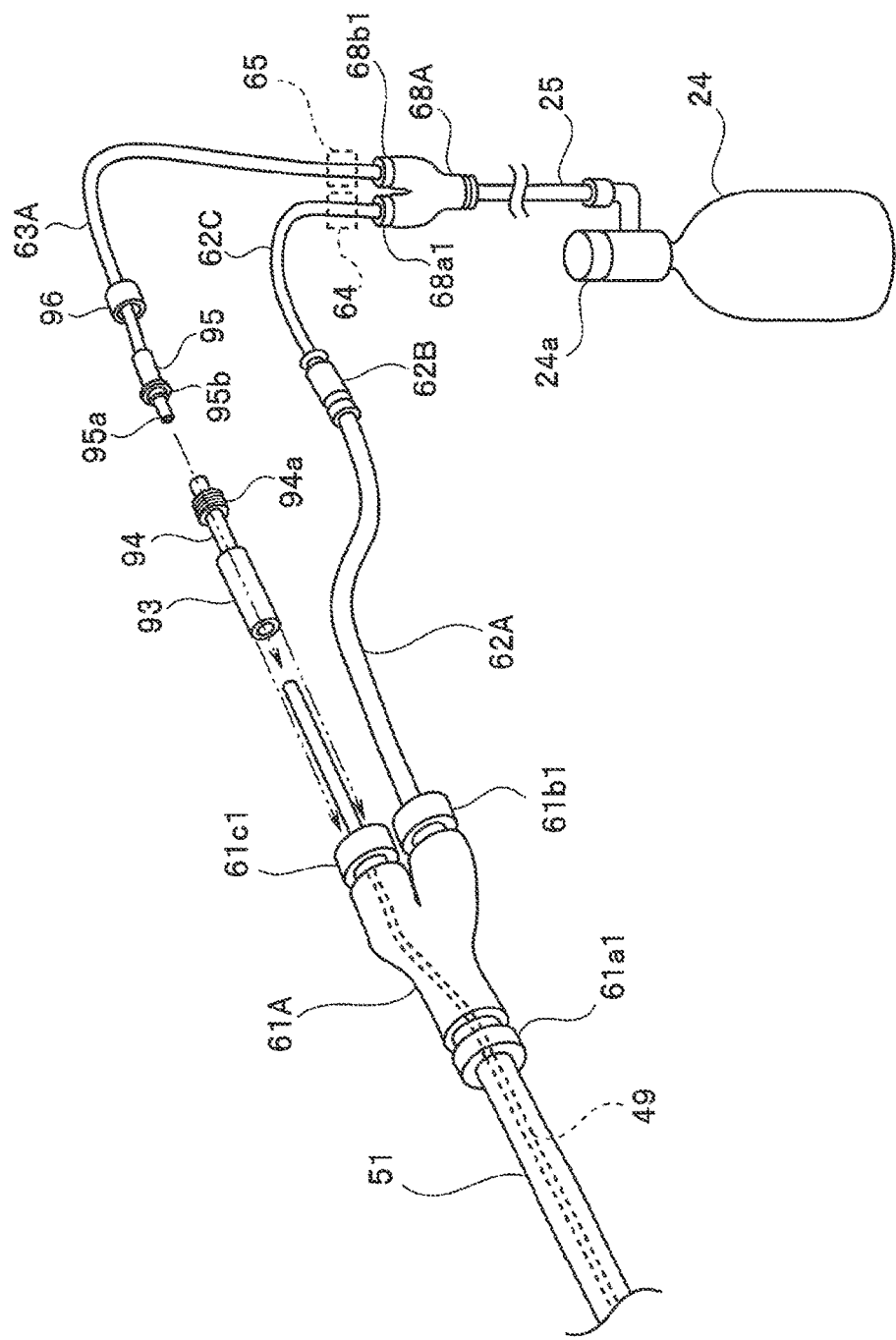
FIG. 10 is a diagram for describing connection and assembly between plural joints and plural conduits in a treatment instrument operation portion 23 according to modification 4 of the embodiment of the present invention.

FIG. 10 is a diagram for describing connection and assembly between plural joints and plural conduits in a treatment instrument operation portion 23 according to modification 4. Note that in FIG. 10, the opening and closing switches 64 and 65 are omitted.

A joint 61A, which is a snap joint, has a connection portion 61a1 connected with the proximal end portion of the sheath member 51. Furthermore, a connection portion 61b1 of the joint 61A is connected with a tube 62A. A proximal end portion of the tube 62A is provided with a connector 62B, which can be detachably connected with one end of a tube 62C. Another end of the tube 62C is connected to a connection portion 68a1 of a joint 68A.

The tube 49 is drawn out of a connection portion 61c1 of the joint 61A. The tube 49 is drawn out of the connection portion 61c1, a proximal end portion of the tube 49 drawn out is inserted in an opening on a distal end side of a tube 93. A threaded portion 94a is formed on an outer circumferential portion on a proximal end side of a pipe sleeve 94 provided on a proximal end portion of tube 93.

The proximal end portion of the pipe sleeve 94 can be connected with a pipe sleeve 95. The pipe sleeve 95 has a nozzle portion 95a in a distal end portion. On a proximal end side of the nozzle portion 95a an annular convex portion 95b is formed on an outer circumferential portion of the nozzle portion 95a, protruding radially outward.

A tube 63A extends out from a proximal end of the pipe sleeve 95. A stop ring 96 is attached to the tube 63A in such a way as to be pivotable around an axis of the tube 63A. A threaded portion configured to be screwed onto a threaded portion 82a is formed in an inner circumferential face of the stop ring 96.

Thus, after the nozzle portion 95a is inserted into an opening in the proximal end portion of the tube 49, when the stop ring 96 is fixed on the threaded portion 94a of the pipe sleeve 94 by screw action, the tube 63A can be connected and fixed to the pipe sleeve 94.

Then, when a distal end portion of the tube 93 is attached to the connection portion 61c1 of the joint 61A, the connection portion 61c1 can be connected in a sealed state.

Thus, modification 4 includes the joint 61A connected with the proximal end portion of the sheath 22, and the joint 61A can be detachably connected with the two tubes 62C and 63A connected to the opening and closing switches 64, 65, which are operation portions.

If the connection portion 61c1 of the joint 61A is not sealed, the air supplied through the tube 62A when the opening switch 64 is operated leaks outside through the connection portion 61c1, and thus the opening action of the treatment unit 21 cannot be performed quickly and reliably.

However, with the configuration of modification 4 described above, since the connection portion 61c1 of the joint 61A is sealed, keeping the air supplied through the tube 62A from leaking out through the connection portion 61c1, the opening action of the treatment unit 21 can be performed quickly and reliably.

According to modification 4, when the treatment instrument is assembled by inserting the tube 49 from the distal end side of the sheath 22, which is an insertion tube portion, a conduit and the like can be mounted easily on the tube 49 in the treatment instrument operation portion 23 later and an interior of the joint 61A can be sealed by the connection portion 61c1, and air can be sent out into the sheath member 1 reliably without leakage.

Also, this configuration allows the sheath member 51 and operation portion 23 to be connected detachably with each other. The operation portion 23 of the treatment instrument apparatus 3 is removed and passed through the treatment instrument channel 31b of the guide apparatus 31 from the distal end side to the proximal end side and then the operation portion 23 on the proximal end side is coupled. This configuration provides the effect of being able to reduce an outside diameter of the guide apparatus 31 even if a grasping portion of the treatment instrument 21 is enlarged.

(Modification 5)

Modification 5 provides an endoscope treatment instrument having a structure which takes into consideration ease of assembly of a distal end portion of the endoscopic treatment instrument according to the embodiment and modifications 1 to 4 described above.

Figure 11:
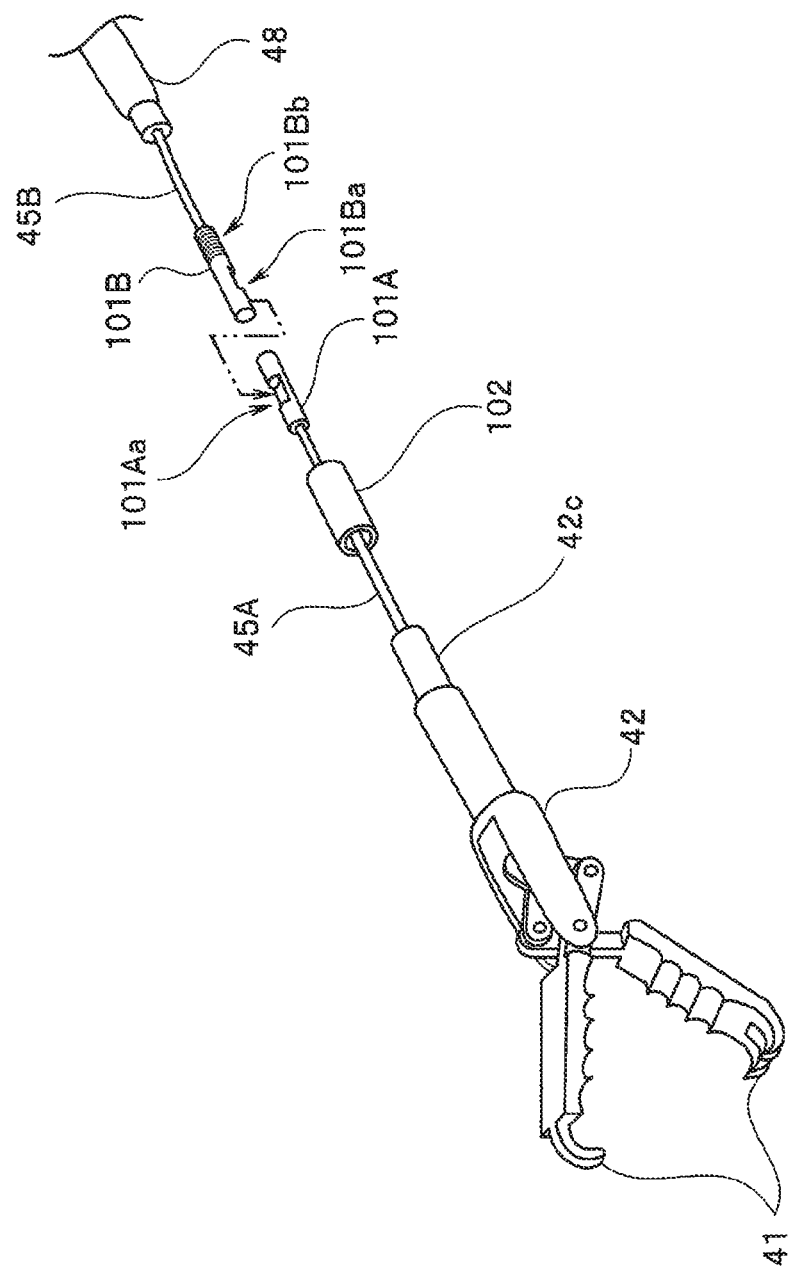
FIG. 11 is a diagram for describing assembly of a portion on a distal end side of a treatment instrument apparatus 3 according to modification 5 of the embodiment of the present invention.

FIG. 11 is a diagram for describing assembly of a portion on a distal end side of a treatment instrument apparatus 3 according to modification 5.

A stepped portion 42c is formed on a proximal end side of the support member 42 and the distal end portion of the sheath member 47 (not illustrated in FIG. 11) is designed to be able to be fitted over the stepped portion 42c. By being attached to the stepped portion 42c, the sheath member 47 is fixed to the support member 42.

A wire 45A extends out from the stepped portion 42c on the proximal end portion of the support member 42. A columnar coupling member 101A having a hook-shaped portion 101Aa is connected and fixed to a proximal end portion of the wire 45A. A stop ring 102 is attached to the wire 45A in such a way as to be pivotable around an axis of the wire 45A. A threaded portion is formed in an inner circumferential face of the stop ring 102.

A wire 45B extends out from the distal end portion of the actuator 48. A columnar coupling member 101B having a hook-shaped portion 101Ba is connected and fixed to a proximal end portion of the wire 45B.

The hook-shaped portion 101Aa of the coupling member 101A and hook-shaped portion 101Ba of the coupling member 101B are shaped such that a convex portion of one of the hook-shaped portions will fit in a concave portion of the other, thereby being engaged with each other, as indicated by chain double-dashed lines in FIG. 11. Thus, when the hook-shaped portion 101Aa of the coupling member 101A and hook-shaped portion 101Ba of the coupling member 101B are engaged with each other, the engaged coupling members 101A and 101B assume a columnar shape as a whole.

A threaded portion 101Bb configured to screw into the threaded portion formed in the inner circumferential face of the stop ring 102 is formed on an outer circumferential portion of the coupling member 101B.

Thus, in a state in which the hook-shaped portion 101Aa of the coupling member 101A and hook-shaped portion 101Ba of the coupling member 101B are engaged with each other, by causing the stop ring 102 to pivot around an axis of the columnar coupling members 101A and 101B so as to cover the coupling members 101A and 101B, the threaded portion formed in the inner circumferential face of the stop ring 102 can be screwed onto threaded portion 101Bb formed on the outer circumferential portion of the coupling member 101B. This makes the treatment unit 21 detachably connected to the sheath member 47.

Thus, with the configuration of modification 5, after inserting the tube 49 from a proximal end side of the sheath 22, which is an insertion tube portion, the treatment instrument apparatus can be assembled easily by mounting the treatment unit 21 on the distal end side of the insertion tube portion 22. Also, this configuration makes the treatment unit of the endoscopic treatment instrument replaceable as well.

Thus, the embodiment and each of the modifications described above provide an endoscopic treatment instrument and endoscope system equipped with an actuator driven by gas and capable of reducing a diameter.

The present invention is not limited to the embodiment described above, and various changes and alterations are possible without departing from the spirit of the invention.

What is claimed is:

1. An endoscopic treatment instrument comprising:
   a sheath having an opening in a distal end;
   an actuator placed in the sheath and driven by a gas supplied via a tube;
   a treatment tool connected with the actuator by a linear member and placed on a distal end side of the opening of the sheath; and
   one or more valves for selectively supplying the gas to either a space between an inner side of the sheath and an outer side of the actuator or to the actuator.

2. The endoscopic treatment instrument according to claim 1, further comprising a gas receiving surface provided on an outer surface of the linear member and configured to receive the gas flowing from a proximal end side to the distal end side of the sheath.

3. The endoscopic treatment instrument according to claim 2, further comprising a rod connected to the treatment tool, wherein the rod comprises an expanded-diameter portion on a distal end side, the expanded-diameter portion being larger in outside diameter than a proximal end side of the rod; and the expanded-diameter portion includes the gas receiving surface.

4. The endoscopic treatment instrument according to claim 3, wherein when the gas is supplied into the sheath and the rod moves to the distal end side, the expanded-diameter portion of the rod protrudes from an opening on a distal end side of a passage hole through which the rod is passed.

5. The endoscopic treatment instrument according to claim 1, wherein:
   the sheath includes a first sheath, a second sheath, and a connector tube sandwiched between the first sheath member and the second sheath member;
   the actuator is placed in the first sheath; and
   the gas in the sheath is suppliable to the distal end side of the sheath via a gap formed between the connector tube and a cover covering the first sheath member and the second sheath.

6. The endoscopic treatment instrument according to claim 1, wherein:
   the sheath includes a first sheath, a second sheath, and a connector tube sandwiched between the first sheath and the second sheath;
   the gas in the sheath is suppliable to the distal end side of the sheath via one or more air vents formed in the connector tube.

7. The endoscopic treatment instrument according to claim 1, wherein:

the sheath includes a first sheath, a second sheath, and a connector tube sandwiched between the first sheath and the second sheath;

the gas in the sheath is suppliable to the distal end side of the sheath via one or more air vents formed in the connector tube; and the connector tube comprises a first portion fixed to a proximal end of the first sheath and a second portion fixed to a distal end of the second sheath.

8. The endoscopic treatment instrument according to claim 1, wherein the treatment tool is a forceps configured to perform an opening and closing action.

9. The endoscopic treatment instrument according to claim 8, wherein the opening and closing action of the forceps is performed by a linkage mechanism configured to convert an advancing action and a retracting action of the linear member running along an axial direction of the sheath into the opening and closing action.

10. The endoscopic treatment instrument according to claim 1, wherein the treatment tool is detachably connected to the sheath.

11. The endoscopic treatment instrument according to claim 1, wherein the one or more valves comprises two valves and the endoscopic treatment instrument further comprising a manifold connected with a proximal end portion of the sheath, wherein the manifold is detachably connected to the two valves.

12. An endoscope system comprising:

the endoscopic treatment instrument according to claim 1;

an endoscope apparatus provided with an insertion portion and a main body portion; and a guide apparatus shaped like a conduit, configured to have flexibility, and provided with first and second insertion channels through which the sheath of the endoscopic treatment instrument and the insertion portion of the endoscope apparatus are passed, respectively.

13. An endoscope system comprising:

the endoscopic treatment instrument according to claim 1; and an endoscope apparatus provided with an insertion portion and a main body portion, wherein the sheath of the endoscopic treatment instrument is configured to be passed through a treatment instrument insertion channel of the insertion portion of the endoscope apparatus.

* * * * *